United States Patent
Lindner et al.

(10) Patent No.: US 8,525,027 B2
(45) Date of Patent: Sep. 3, 2013

(54) MODULAR LEAD INTERCONNECTOR

(75) Inventors: Gerald G. Lindner, Lino Lakes, MN (US); Paulette C. Olson, Eagan, MN (US); Darren A. Janzig, Center City, MN (US); Chris J. Paidosh, St. Anthony, MN (US)

(73) Assignee: Medtronic, Inc., Minneapolis, MN (US)

( * ) Notice: Subject to any disclaimer, the term of this patent is extended or adjusted under 35 U.S.C. 154(b) by 463 days.

(21) Appl. No.: 12/937,644

(22) PCT Filed: Jan. 23, 2009

(86) PCT No.: PCT/US2009/031785
§ 371 (c)(1),
(2), (4) Date: Nov. 24, 2010

(87) PCT Pub. No.: WO2009/131725
PCT Pub. Date: Oct. 29, 2009

(65) Prior Publication Data
US 2011/0165785 A1    Jul. 7, 2011

Related U.S. Application Data

(60) Provisional application No. 61/046,530, filed on Apr. 21, 2008.

(51) Int. Cl.
*H01B 17/08* (2006.01)
(52) U.S. Cl.
USPC ...................................... 174/88 R

(58) Field of Classification Search
USPC ............................... 174/88 R, 84 C; 607/122
See application file for complete search history.

(56) References Cited

U.S. PATENT DOCUMENTS

| | | | | |
|---|---|---|---|---|
| 3,406,247 A * | 10/1968 | Parsons | ........................ | 174/88 R |
| 3,842,191 A * | 10/1974 | Neale, Sr. | .................... | 174/88 R |
| 5,021,611 A * | 6/1991 | Amano | ........................ | 174/88 R |
| 6,249,708 B1 * | 6/2001 | Nelson et al. | ................. | 607/122 |
| 6,813,521 B2 | 11/2004 | Bischoff et al. | | |
| 7,130,699 B2 | 10/2006 | Huff et al. | | |
| 7,184,838 B2 | 2/2007 | Cross | | |
| 7,292,894 B2 * | 11/2007 | Belden | ........................ | 607/122 |
| 7,519,432 B2 | 4/2009 | Bolea et al. | | |
| 7,546,163 B2 | 6/2009 | Bischoff et al. | | |
| 2005/0027325 A1 | 2/2005 | Lahti et al. | | |

FOREIGN PATENT DOCUMENTS

EP    1847290    10/2007

OTHER PUBLICATIONS

PCT/US09/31785: Search Report and Written Opinion dated Apr. 27, 2009.

* cited by examiner

*Primary Examiner* — Phuong Dinh

(57) ABSTRACT

An end interconnector for one or both ends of a lead body of an electrical lead for an implantable medical device. The interconnector has an insulative body having a receptacle at its first end for each of a plurality of wire filars from the lead body, and a receiver at its second end for each of a plurality of connection wires extending from the medical device, such as an electrode tip. The interconnector provides electrical connection between the plurality of wire filars and the plurality of connection wires.

20 Claims, 5 Drawing Sheets

MODULAR LEAD INTERCONNECTOR

This application claims the benefit of and is a U.S. National Stage filing under 35U.S.C. 371 of copending PCT Application Serial No. PCT/US2009/31785, filed Jan. 23, 2009, which in turn claims the benefit of U.S. Provisional Application No. 61/046,530, filed Apr. 21, 2008, "Modular Lead Interconnector," the disclosure of all of the above which is incorporated by reference herein in its entirety.

FIELD

This application relates to medical devices, more particularly implantable leads and lead extensions for delivering electrical signals.

BACKGROUND

Implantable electrical signal generators, such as pacemakers, defibrillators, neurostimulators, and the like, have been used to treat a variety of diseases. Such devices generate electrical signals that are transferred to a patient's tissue through electrodes present on a distal end portion of a lead. The proximal end portion of a lead, connected to a signal generator, typically contains a number of connector rings corresponding to the number of electrodes. Conductors, also referred to as wire filars or merely filars, run within and along the lead body and electrically couple the connectors to the electrodes.

One particular type of implantable device is an implantable neurological stimulation system that can be used to treat conditions such as pain, movement disorders, pelvic floor disorders, gastroparesis, and a wide variety of other medical conditions. The neurostimulation system typically includes a neurostimulator, a stimulation lead, and an optional lead extension. As an example, the neurostimulator system can be an Itrel II™ Model 7424 or an Itrel 3™ Model 7425 available from Medtronic, Inc., in Minneapolis, Minn., that can be used to treat conditions such as pain, movement disorders and pelvic floor disorders. The neurostimulator is typically connected to a stimulation lead that has one or more electrodes to deliver electrical stimulation to a specific location in the patient's body.

BRIEF SUMMARY

The present disclosure is directed to implantable leads and lead extensions and methods of making the leads and extensions. A lead end interconnector module is present at least one end of the lead or extension.

For example, an implantable medical device, such as a lead or lead extension, having a body is described. The body includes an external surface, a proximal end portion configured to be at least partially received by an apparatus, and distal end portion configured to be attached to an electrode tip. The implantable medical device further includes a conductive member at the distal end portion of the body and an electrical contact at the proximal end portion of the body. The electrical contact is electrically coupled to the conductive member and is positioned such that, when received by the apparatus, at least a portion of the apparatus is capable of electrically coupling to the electrical contact.

In one exemplary embodiment, this disclosure is directed to an end interconnector for attachment to a lead body of an electrical lead for an implantable medical device, the end interconnector configured to engage with one of the proximal end or the distal end of the lead body. The interconnector has a body having a surface, a first end and a second end, the body first end having a receptacle for each of a plurality of wire filars from the lead body, and the body second end having a receiver for each of a plurality of connection wires extending to the medical device. The interconnector includes an electrical connection region configured to provide electrical connection between the plurality of wire filars and the plurality of connection wires.

The interconnector may have a plurality of longitudinal receptacles for receiving the plurality of wire filars; these receptacles may be present within the surface of the interconnector body. In other embodiments, the receptacles are passages in the interconnector body. In some embodiments, the receptacles are longitudinally spiraled.

In another exemplary embodiment, the disclosure is directed to an electrical lead for an implantable medical device, the lead comprising a lead body having a proximal end and a distal end and a plurality of electrically conductive wire filars extending from the proximal end to the distal end. An end interconnector is electrically engaged with the wire filars at one or both ends of the lead body. Electrically engaged to the interconnector at the lead's distal end may be a medical device, such as an electrode tip. Electrical leads may be provided to the user (e.g., a doctor or surgeon) with the end interconnector engaged with the medical device, or, the user may attach the desired medical device to the interconnector.

In yet another exemplary embodiment, the disclosure is directed to a method of assembling an electrical lead. The method includes providing a lead body having a plurality of wire filars extending from a distal end to a proximal end, placing the wire filars from either the distal end or the proximal end of the lead body into the receptacles at the first end of the interconnector, and electrically connecting the wire filars to the electrical connection region. The method may include attaching a second interconnector to the other end of the lead body. These methods may be done at the manufacturing facility of the lead. Further methods include attaching a medical device, such as an electrode tip, to an end of the lead; these methods may be done at the manufacturing facility or at the point of use.

These and other advantages will be readily understood from the following detailed descriptions when read in conjunction with the accompanying drawings.

The drawings are not necessarily to scale. Like numbers used in the figures refer to like components, steps and the like. However, it will be understood that the use of a number to refer to a component in a given figure is not intended to limit the component in another figure labeled with the same number.

DETAILED DESCRIPTION

In the following detailed description, reference is made to the accompanying drawing that form a part hereof, and in which are shown by way of illustration several specific embodiments of devices, systems and methods. It is to be understood that other embodiments are contemplated and may be made without departing from the scope of spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used herein, "proximal" and "distal" refer to positions relative to an implantable pulse or signal generator. For example, a proximal portion or end of a lead is a portion or end nearer a signal generator (e.g., a neurostimulator), and a distal portion or end is a portion or end further from the signal generator.

The present disclosure relates to implantable leads and lead extensions and methods of making the leads and extensions. A lead end interconnector module is present at least one end of the lead or extension. The lead end interconnector module facilitates the manufacture of leads and their connection to a signal generator and/or a medical device such as an electrode tip.

Figure 1:
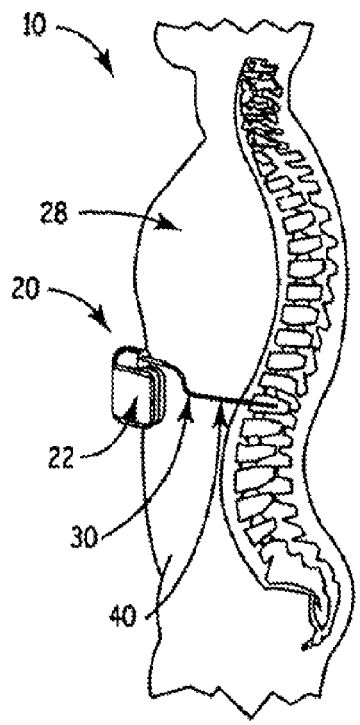
FIG. 1 is a diagrammatic representation of a general environmental view for a neurostimulation system embodiment.

Referring to the figures, FIG. 1 shows a general environmental view 10 for an implantable neurostimulation system. Neurostimulation systems are used to treat conditions such as pain, movement disorders, pelvic floor disorders, gastroparesis, and a wide variety of other medical conditions. Neurostimulation system 20 includes a neurostimulator 22, a stimulation lead extension 30, and a stimulation lead 40. Neurostimulator 22 is typically implanted subcutaneously in a patient's body 28 at a location selected by the clinician; although FIG. 1 illustrates neurostimulator 22 implanted in the patient's abdomen, other locations are suitable. Stimulation lead 40 is typically fixed in place terminating near the desired location selected by the clinician (e.g., in the brain or spinal cord) using a device such as an adjustable anchor.

Figure 2:
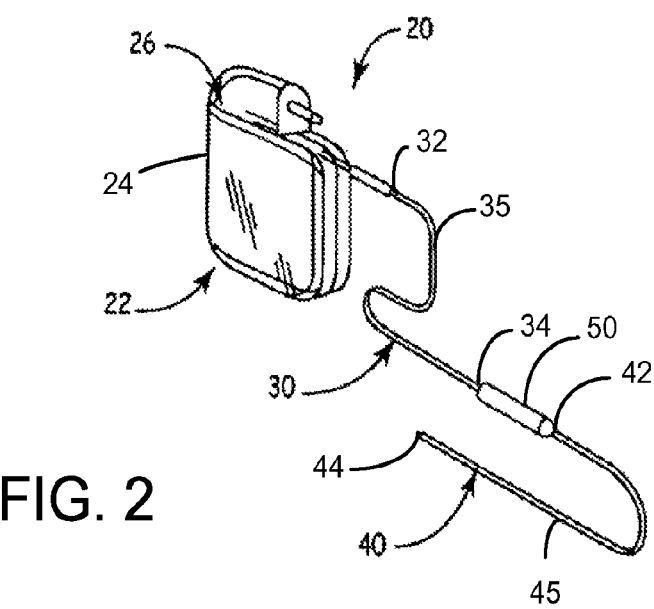
FIG. 2 is a perspective view of the neurostimulation system embodiment of FIG. 1.

FIG. 2 shows an enlarged view of implantable neurostimulation system 20 having implantable neurostimulator 22, stimulation lead 40, and lead extension 30. Implantable neurostimulator 22 has a housing 24, a power supply (e.g., a battery) within housing 24, and stimulation electronics coupled to the power supply and coupled to a connector block 26, which is also known as a terminal block. Stimulation lead 40 has a lead proximal end 42, a lead distal end 44 and a lead body 45. At lead distal end 44 is medical device such as an electrode tip having at least one stimulation electrode (not illustrated). Lead extension 30 has an extension proximal end 32, an extension distal end 34, and an extension body 35. Lead proximal end 42 connects to lead extension distal end 34 at connector 50; either or both lead proximal end 42 or extension distal end 34 may include an electrode tip that engages with connector 50.

Lead 40 and lead extension 30 provide electrical communication from neurostimulator 22 to the electrode tip at distal end 44. Lead distal end 44 contains at least one electrode but in most embodiments has a plurality of such electrodes (e.g., 4, 8, 16, etc.). Extending through lead 40 and lead extension 30 are electrically conducting wire, often referred to as filars or wire filars, that couple neurostimulator 22 to the electrode tip and its electrode(s). The wire filars may, for example, be stranded (made up of many small wires), braided-stranded or "BSW" (braided of many small wires), or solid or monofilament. Extending over and covering the wire filars is an electrically insulating jacket or sheath. Typically, this jacket is a polymeric material, such as ethylene tetrafluoroethylene (ETFE), polytetrafluoroethylene (PTFE), silicone rubber or polyurethane. Other materials that act as electrical insulators can be used. In some embodiments, a shielding layer or jacket may be present, optionally over the insulating jacket. An example of one suitable shielding layer is described in U.S. Patent Application Publication No. 2005/0222658.

The invention of this disclosure is directed to an end piece interconnector for a lead structure, for either or both proximal end 42 or distal end 44 of lead 40, or proximal end 32 or distal end 34 of lead extension 30. It should be understood that the following discussion of the modular end pieces or interconnects of this invention makes reference to "lead", "leads", "lead body", and the like, generically, and that this discussion is not limiting to positions or uses of the end interconnects of this disclosure, but that they may be used at any location. It should also be understood that the end piece interconnector and the lead structures could be used with applications other than just neurostimulators.

Figure 3:
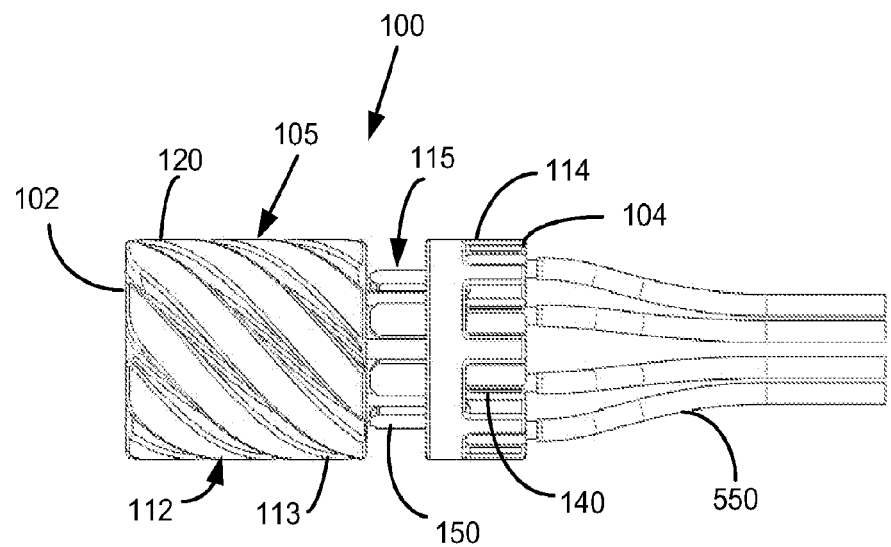
FIG. 3 is a perspective view of an exemplary embodiment of a lead end interconnector module according to this disclosure.

Referring to FIG. 3, an exemplary embodiment of a lead end interconnector is illustrated as interconnector 100. Interconnector 100 has a body 105, usually made from a non-conductive or insulative material (e.g., a polymeric material (preferably medical grade polymeric material) such as polyurethane, polyethylene, polysulfone, polyetheretherketone, silicone rubber, or combinations thereof) having a first end 102 and an opposing second end 104. First end 102 is configured to connect with a lead body (e.g., lead body 45) and second end 104 is configured to connect with a medical device, such as an electrode tip.

Interconnector 100 includes a lead end region 112 proximate first end 102 and an extension region 114 proximate second end 104. Lead end region 112 has an outer surface 113. Present between lead end region 112 and extension region 114 is an electrical connection region 115.

Present in lead end region 112 are a plurality of receptacles 120, at least one for each wire filar of the lead body to which interconnector 100 is to be connected. Receptacles 120 are configured to direct the wire filars to electrical connection region 115. In this embodiment, receptacles 120 are channels within surface 113 of lead end region 112, in particular, eight channels are molded or otherwise formed in end region 112. Receptacles 120 spiral around lead end region 112, extending longitudinally from first end 102 to electrical connection region 115.

Electrical connection region 115 includes junction areas 150, at least one for each wire filar of the lead body to which interconnector 100 is to be connected, and typically the same number of junction areas 150 as receptacles 120. Junction areas 150 are in electrical connection with extension region 114, which includes a plurality of receivers 140, at least one for each wire filar of the lead body to which interconnector 100 is to be connected, and typically the same number of receivers 140 as receptacles 120. In this embodiment, interconnector 100 has eight receivers 140. Either or both receivers 140 and junction areas 150 may be of a conductive material, such as, but not limited to, titanium, stainless steel, tantalum, palladium, a cobalt-nickel-chromium alloy, a platinum-iridium alloy, or a palladium alloy. Either or both receivers 140 and junction areas 150 may include a weldable or solderable material.

In FIG. 3, extending from receivers 140 are illustrated a plurality of electrode connection wires 550. Electrode wires 550 provide electrical connection to a medical device, such as an electrode tip, and in some embodiments, are considered as part of the medical device, e.g., electrode tip. Connection wires 550 may be removably connected to receivers 140. In this embodiment, eight electrode connection wires 550 are illustrated. In many embodiments, the number of connection wires 550 is the same as the number of wire filars of the lead body to which interconnector 100 is to be connected.

Figure 4:
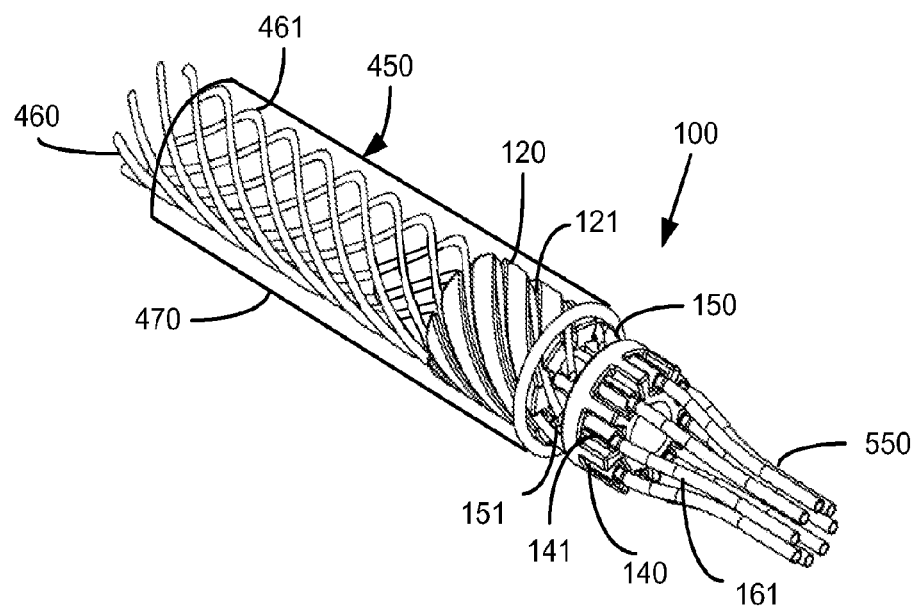
FIG. 4 is a perspective view of the lead end interconnector module of FIG. 3 electrically connected to a lead body.

FIG. 4 illustrates interconnector 100 connected to a lead body. Lead body 450 has a plurality of electrically conductive wire filars 460 extending longitudinally through lead body 450 and covered by an insulative jacket 470. In FIG. 4, eight wire filars 460 are illustrated as a helical extension. Each of the eight wire filars 460 has a corresponding receptacle 120, contact area 150 and receiver 140, and corresponding electrode wire 550 for connecting to a medical device. For example, wire filar 461 is present in receptacle 121 and terminates at contact area 151. Electrically connected to contact area 151 is connection pad 141, from which extends electrode wire 161.

To connect lead body 450 to interconnector 100, each wire filar 460 is inserted into a corresponding receptacle 120 and channeled to junction area 150 in connecting region 115. Wire filar 460 is secured within junction area 150 and electrical connection is made; this may be done, for example, by welding (e.g., ultrasonic welding) or soldering, by crimping, staking, or by a quick-connect or snap fit or other suitable mechanism. To connect a medical device, e.g., an electrode tip, to interconnector 100, each electrode connection wire 550 is attached to a corresponding receiver 140, in electrical connection to junction area 150. Electrode wire 550 is secured to receivers 140 and electrical connection is made; this may be done, for example, by welding or soldering, by crimping, staking, or by a quick-connect or snap fit.

Figure 5:
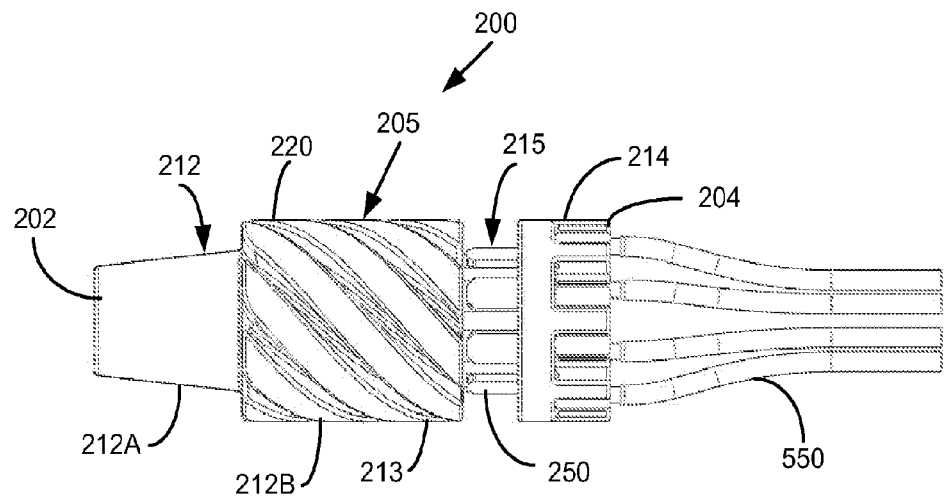
FIG. 5 is a side view of an exemplary embodiment of a lead end interconnector module according to this disclosure.
Figure 6:
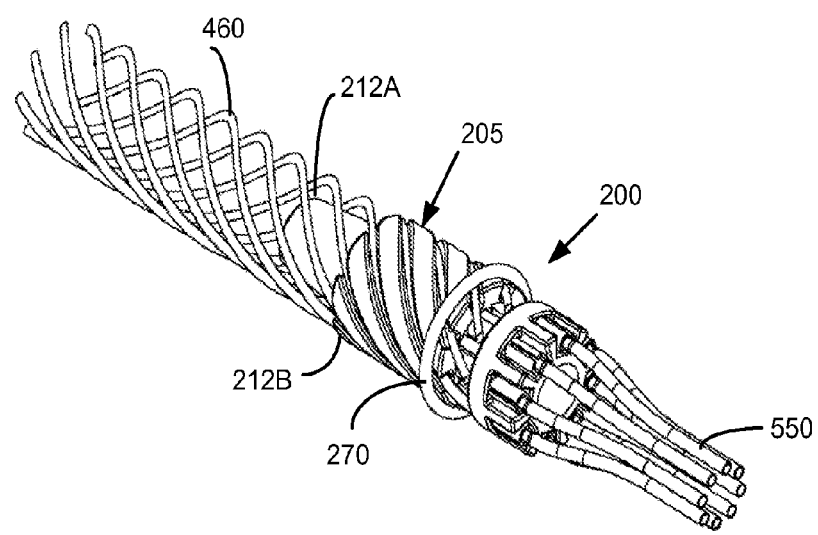
FIG. 6 is a perspective view of the lead end interconnector module of FIG. 5 electrically connected to a lead body.

An exemplary embodiment of an end interconnector having longitudinally spiraled surface receptacles is illustrated in FIGS. 5 and 6 as end interconnector 200. The various features of interconnector 200 are the same as or similar to interconnector 100 of FIGS. 3 and 4, unless otherwise specified.

End interconnector 200 has a body 205 having a first end 202 and an opposing second end 204. Interconnector 200 includes a lead end region 212 proximate first end 202 and an extension region 214 proximate second end 204. Present between lead end region 212 and extension region 214 is electrical connection region 215. Lead end region 212 has a guide portion 212A and an engagement portion 212B having a surface 213. Present in engagement portion 212B are a plurality of receptacles 220, at least one for each wire filar of the lead body to which interconnector 200 is to be connected. Receptacles 220 are configured to direct the wire filars to electrical connection region 215 and junction areas 250.

Guide portion 212A extends from engagement portion 212B and facilitates engagement of interconnector 200 with the wire filars during assembly of interconnector 200 with the engaging lead body by providing an alignment structure, e.g., a centering structure. Guide portion 212A of interconnector 200 is a conical structure, having a tapered surface. In FIG. 6, interconnector 200 is illustrated connected to wire filars 460 of a lead body. The plurality of spiraling electrically conductive wire filars 460 wrap around guide portion 212A and engagement portion 212B. Guide portion 212A is encased by wire filars 460 and typically by the sheath (not illustrated) of the lead body.

In FIG. 6, an optional retainment system 270 is shown on interconnector 200, to better hold wire filars 460 in receptacles 220 and in electrical connection region 215. Retainment system 270 may be temporarily positioned on interconnector 200, for example, to maintain wire filars 460 in receptacles 220 until permanently positioned (e.g., welded or soldered). In this embodiment, retainment system 270 is a ring-type structure extending around lead end region 212.

Figure 7:
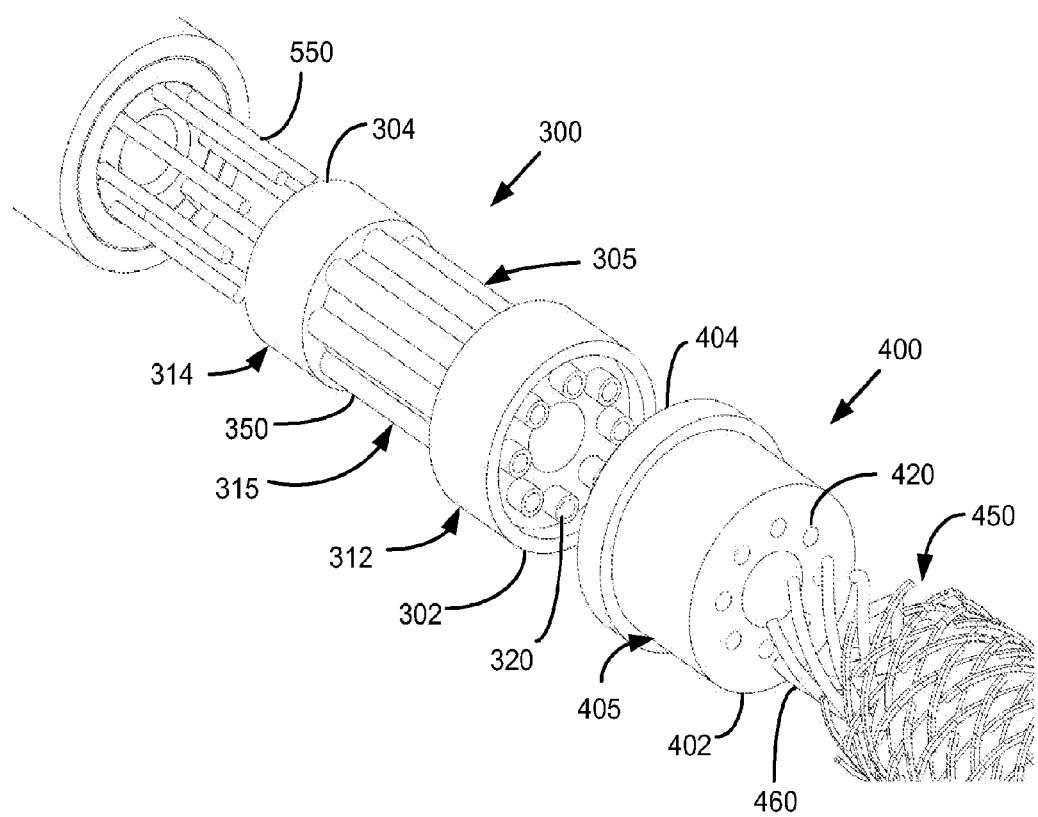
FIG. 7 is an exploded perspective view of an exemplary embodiment of a lead end interconnector module according to this disclosure, including a transition member positioned between the interconnector and the lead body.

An exemplary embodiment of an end interconnector, this one having longitudinally extending enclosed receptacles, is illustrated in FIG. 7 as end interconnector 300. The various features of interconnector 300 are the same or similar to interconnector 100 of FIGS. 3 and 4 and interconnector 200 of FIGS. 5 and 6, unless otherwise specified.

End interconnector 300 has a body 305 having a first end 302 and an opposing second end 304. Interconnector 300 includes a lead end region 312 proximate first end 302 and an extension region 314 proximate second end 304. Present between lead end region 312 and extension region 314 is an electrical connection region 315. Extending through body 305, from lead end region 312 through electrical connection region 315 to extension region 314 are a plurality of receptacles 320, at least one for each wire filar of the lead body to which interconnector 300 is to be connected. Receptacles 320 are configured to direct the wire filars to junction areas 350 or electrical connection region 315.

For interconnector 300, receptacles 320 extend through lead end region 312 to junction areas 350. That is, receptacles 320 are not on an outer surface of lead end region 312 as in the previous embodiments of interconnectors 100, 200, but pass through an inner portion of lead end region 312. Receptacles 320 extend the length of interconnector 300, from first end 302 to second end 304. At second end 304, receptacles 320 are configured to accept electrode connector wires 550 from an electrode tip or other medical device.

In interconnector 100, 200 described above, junction areas 150, 250 of electrical connection regions 115, 215 are exposed; that is, junction areas 150, 250 are present on an outer surface of interconnector 100, 200. For interconnector 300, conversely, the electrical junction areas 350, where wire filars from a lead body and electrode connector wires from a medical device such as an electrode tip make electrical connection, are within tubular receptacles 320. Receptacles 320 and/or junction areas 350 may be of a conductive material, such as, but not limited to, titanium, stainless steel, tantalum, palladium, a cobalt-nickel-chromium alloy, a platinum-iridium alloy, or a palladium alloy. Either or both receptacles 320 and/or junction areas 350 may be of a weldable or solderable material. In some embodiments, the junction areas 350 are part of or integral with receptacles 320.

Interconnector 300 includes an optional transition member to facilitate the engagement of wire filars 460 with receptacles 320. In FIG. 7, positioned adjacent first end 302 is transition member 400. Transition member 400 has a body 405 having a first end 402 and an opposite second end 404. In FIG. 7, second end 404 engages with first end 302 of interconnector 300, and may be permanently affixed thereto. Extending through body 405 is a plurality of receptacles 420. In this embodiment, receptacles 420 pass longitudinally through body 405 from first end 402 to second end 404 at an angle (e.g., at an angle of about 20 degrees); that is, receptacles 420 do not pass through parallel to the longitudinal axis of body 405.

Transition member 400 provides a transition for wire filars 460 of lead body 450 to interconnector 300. In lead body 450, wire filars 460 spiral longitudinally at an angle of about 45 degrees, and in interconnector 300, electrical connection region 315 holds the wire filars parallel to its longitudinal axis. Transition member 400 eases the progression from 45 degrees to 0 degrees for wire filars 460.

In FIG. 7, interconnector 300 and transition member 400 are illustrated in preparation for connection to lead body 450 and a plurality of electrode connection wires 550. Electrode wires 550 provide electrical connection to the electrode tip and in some embodiments, as illustrated in FIG. 8.

To connect lead body 450 to interconnector 300 using transition member 400, transition member 400 is attached to first end 302 of interconnector 300. Each wire filar 460 is inserted into a corresponding receptacle 420 and fed through to junction area 350. In some embodiments, a wire filar 460 may be fed into receptacle 420 prior to attaching transition member 400 to interconnect 300. Wire filar 460 is secured within junction area 350 and electrical connection is made; this may be done, for example by welding or soldering.

Figure 8:
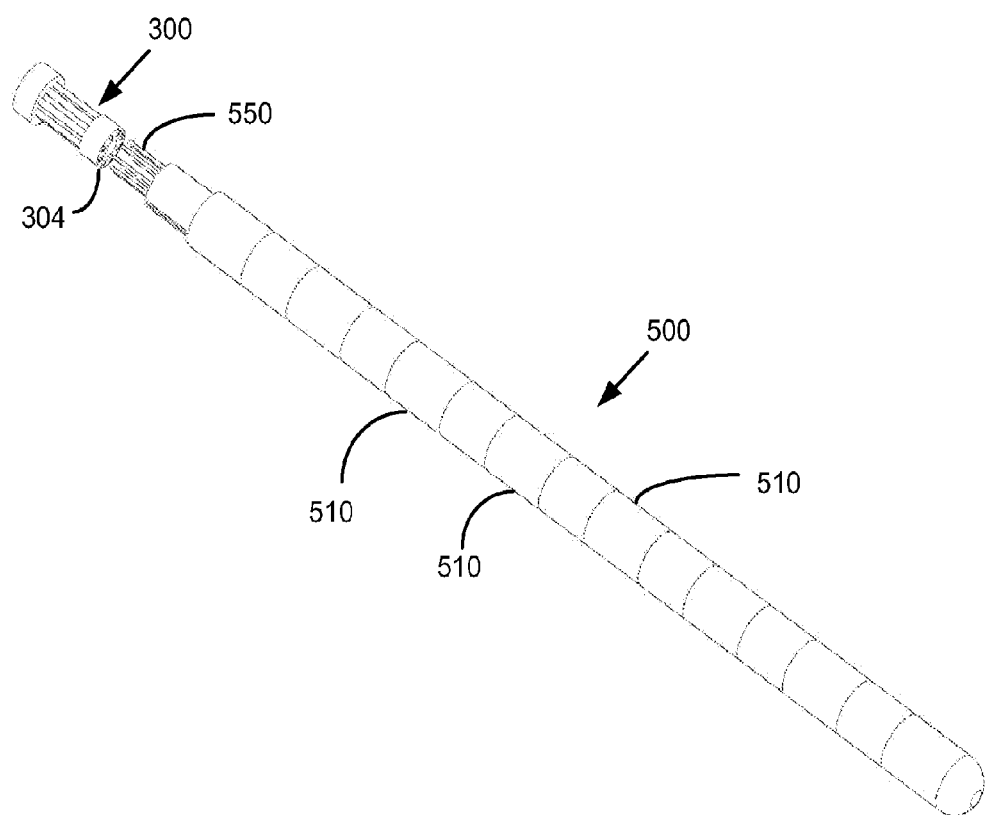
FIG. 8 is a perspective view of an electrode tip positioned for electrical connection with the lead end interconnector module of FIG. 7.

An electrode tip 500 is illustrated in FIG. 8, poised for connection to interconnector 300. Electrode tip 500 has eight electrode areas 510, one for each electrode wire 550 extending from tip 500. To connect electrode tip 500 to interconnector 300, each electrode wire 550 is inserted into a corresponding receptacle 320 and fed through to junction area 350. Electrode wire 550 is secured within junction area 350 and electrical connection is made; this may be done, for example by welding or soldering.

The various embodiments of the MODULAR LEAD INTERCONNECTOR described above can be used at one or both ends of a lead body. The interconnectors may additionally or alternately be used for lead extensions. Although various embodiments of the MODULAR LEAD INTERCONNECTOR have been disclosed, one skilled in the art will appreciate that the present disclosure can be practiced with embodiments other than those described and illustrated. For example, the interconnector may be configured for different numbers of wire filars and electrode wires, for example, 4, 6, 12, 16, 32, etc. Also for example, the interconnector may be used with other lead body configurations, having, for example, different filar numbers or configurations, or, for example, various jackets or sheaths. The medical device may be, for example, an electrode tip other than illustrated.

The disclosed exemplary embodiments are presented for purposes of illustration and not limitation.

What is claimed is:

1. An end interconnector for attachment to a lead body of an electrical lead for an implantable medical device, the end interconnector configured to engage with one of the proximal end or the distal end of the lead body, the interconnector comprising:
   (a) a body having a surface, a first end and a second end, the body first end having a longitudinally spiraled receptacle for each of a plurality of wire filars from the lead body, and the body second end having a receiver for each of a plurality of connection wires extending the medical device; and
   (b) an electrical connection region, configured to provide electrical connection between the plurality of wire filars and the plurality of connection wires.

2. The end interconnector of claim 1, wherein the longitudinally spiraled receptacles are longitudinally spiraled channels in the surface of the interconnector body.

3. The end interconnector of claim 1, wherein the longitudinally spiraled receptacles are longitudinally spiraled passages in the interconnector body.

4. The end interconnector of claim 3, wherein the longitudinally spiraled passages comprise an electrically conductive material.

5. The end interconnector of claim 1, wherein the end interconnector comprises a transition member and a connection hub, and wherein the transition member comprises the longitudinally spiraled receptacles.

6. The end interconnector of claim 5, wherein the connection hub comprises the electrical connection region.

7. The end interconnector of claim 6, wherein the electrical connection region in the connection hub comprises straight passages.

8. The end interconnector of claim 1, wherein the body comprises a medical grade polymeric material.

9. The end interconnector of claim 8, wherein the polymeric material comprises polyurethane, polyethylene, polysulfone, polyetheretherketone, silicone rubber, or combinations thereof.

10. The end interconnector of claim 1, wherein the electrical connection region comprises a weldable material.

11. The end interconnector of claim 1, wherein the electrical connection region comprises titanium, stainless steel, tantalum, palladium, a cobalt-nickel-chromium alloy, a platinum-iridium alloy, or a palladium alloy.

12. An electrical lead for an implantable medical device, the lead comprising:
   (a) a lead body comprising
      (i) a proximal end and a distal end;
      (ii) a plurality of electrically conductive wire filars extending from the proximal end to the distal end;
   (b) an end interconnector electrically engaged with one of the proximal end or the distal end of the lead body, the end interconnector comprising:
      (i) a body having a surface, a first end and a second end, the body first end having a longitudinally spiraled receptacle for each of a plurality of wire filars from the lead body, and the body second end having a receiver for each of a plurality of connection wires extending the medical device; and
      (ii) an electrical connection region, configured to provide electrical connection between the plurality of wire filars and the plurality of connection wires.

13. The electrical lead of claim 12, comprising a first end interconnector electrically engaged with the proximal end of the lead body and a second end interconnector electrically engaged with the distal end of the lead body.

14. The electrical lead of claim 12 further comprising an electrode tip electrically connected to the proximal end of the lead.

15. The electrical lead of claim 12 further comprising an electrode tip electrically connected to the distal end of the lead.

16. A method of assembling the electrical lead for an implantable medical device, comprising:
   providing a lead body having a plurality of wire filars extending from a distal end to a proximal end;
   providing an end interconnector comprising:

(a) a body having a surface, a first end and a second end, the body first end having a longitudinally spiraled receptacles for receiving each of a plurality of wire filars from the lead body, and the body second end having a receiver for each of a plurality of connection wires extending the medical device; and (b) an electrical connection region, configured to provide electrical connection between the plurality of wire filars and the plurality of connection wires;

placing the wire filars from either the distal end or the proximal end of the lead body into the longitudinally spiraled receptacles at the first end of the interconnector; and electrically connecting the wire filars to the electrical connection region.

17. The method of claim 16, comprising:

placing the wire filars of the distal end of the lead body into the receptacles at the first end of the interconnector; and placing the wire filars of the proximal end of the lead body into the receptacles at the first end of a second interconnector.

18. The method of claim 16, wherein electrically connecting the wire filars to the electrical connection region comprises:

connecting the wire filars to the electrical connection region by welding, soldering, crimping, staking, ultrasonics, a quick-connect or snap fit.

19. The method of claim 18, wherein electrically connecting the wire filars to the electrical connection region comprises:

welding the wire filars to the electrical connection region.

20. The method of claim 16 further comprising:

placing electrode connection wires from an electrode tip into the receivers at the second end of the interconnector; and electrically connecting the electrode connection wires to the electrical connection region.

\* \* \* \* \*